US009795349B2

(12) United States Patent
Lou et al.

(10) Patent No.: US 9,795,349 B2
(45) Date of Patent: Oct. 24, 2017

(54) METHOD FOR SETTING SCANNING PROTOCOL AND APPARATUS THEREOF

(71) Applicant: Shenyang Neusoft Medical Systems Co., Ltd., Shenyang (CN)

(72) Inventors: Shanshan Lou, Shenyang (CN); Changkun Liu, Shenyang (CN)

(73) Assignee: SHENYANG NEUSOFT MEDICAL SYSTEMS CO., LTD., Shenyang (CN)

( * ) Notice: Subject to any disclaimer, the term of this patent is extended or adjusted under 35 U.S.C. 154(b) by 148 days.

(21) Appl. No.: 14/798,480

(22) Filed: Jul. 14, 2015

(65) Prior Publication Data

US 2016/0007942 A1 Jan. 14, 2016

(30) Foreign Application Priority Data

Jul. 14, 2014 (CN) .......................... 2014 1 0334820

(51) Int. Cl.
*A61B 6/00* (2006.01)
*A61B 6/03* (2006.01)

(52) U.S. Cl.
CPC ............ *A61B 6/469* (2013.01); *A61B 6/032* (2013.01); *A61B 6/488* (2013.01); *A61B 6/545* (2013.01); *A61B 6/505* (2013.01); *A61B 6/5235* (2013.01)

(58) Field of Classification Search
CPC .. A61B 6/00; A61B 6/03; A61B 6/032; A61B 6/469; A61B 6/488; G06T 7/00; G06T 7/0081; G06T 2207/10081; G01N 23/04
USPC .................. 378/62, 207, 4, 8, 901
See application file for complete search history.

(56) References Cited

U.S. PATENT DOCUMENTS

| 6,195,409 | B1 | 2/2001 | Chang et al. |
| 2011/0158490 | A1 | 6/2011 | Cong et al. |
| 2013/0177224 | A1 | 7/2013 | Papageorgiou et al. |
| 2015/0073255 | A1 | 3/2015 | Liu et al. |

FOREIGN PATENT DOCUMENTS

| CN | 102113897 A | 7/2011 |
| CN | 102525525 A | 7/2012 |
| CN | 103494613 A | 1/2014 |

OTHER PUBLICATIONS

The first Office Action issued on Nov. 25, 2015 regarding the Chinese priority patent application (Appl.No. 201410334820.4).

*Primary Examiner* — Jurie Yun
(74) *Attorney, Agent, or Firm* — Kilpatrick Townsend & Stockton LLP

(57) ABSTRACT

A method for setting a scanning protocol and an apparatus thereof are provided. The method includes: creating a plain film positioning image; receiving a point or a line or a region of interest on the plain film positioning image input by an operator; generating a region to be matched, based on the point or the line or the region of interest; determining whether there is pre-stored reference image having a matching degree greater than a preset threshold by comparing pre-stored reference images with the region to be matched; obtaining a reference image in the case that the reference image has a matching degree greater than the preset threshold; selecting a scanning protocol corresponding to the reference image based on a preset correspondence between reference images and scanning protocols; and completing a setting of the scanning protocol in the case that there is the scanning protocol corresponding to the reference image.

10 Claims, 4 Drawing Sheets

METHOD FOR SETTING SCANNING PROTOCOL AND APPARATUS THEREOF

CROSS REFERENCE OF RELATED APPLICATION

The present application claims the priority to Chinese Patent Application No. 201410334820.4, entitled "METHOD FOR SETTING SCANNING PROTOCOL AND APPARATUS THEREOF", filed on Jul. 14, 2014 with the State Intellectual Property Office of the PRC, which is incorporated herein by reference in its entirety.

BACKGROUND

Before performing a CT scanning on a clinical patient, an operator of a CT apparatus needs to set a series of scanning parameters of a scanning protocol for the CT apparatus based on the diagnosis of a doctor. The scanning protocol determines a data acquisition way, an image reconstruction way, a radiation dose and so on required during the scanning on the patient.

Since the parameters of a scanning protocol are associated with and constrained by each other, significantly different scanning doses may be caused and images finally obtained through scanning may be of significantly different qualities due to different combination ways of the parameters. Hence, the manufacturer of the CT apparatus and the personnel of the related clinical application may establish a series of scanning protocols in advance based on various actual diagnosing requirements and store the scanning protocols in advance. The operator of the CT apparatus may select from the stored scanning protocols based on corresponding diagnosing requirements.

However, since the types of the clinical diagnosing are diverse, it is troublesome and time-consuming to select a suitable scanning protocol from the pre-established various scanning protocols based on the diagnosis of the doctor. In addition, once the clinical patient is scanned and a positioning plain film is obtained, if the operator of the CT apparatus spends a lot of time to select the scanning protocol subsequently, the location of lesion of the patient may alter during the selection of the scanning protocol with an increasing probability, thereby influencing the accuracy for the subsequent scanning and positioning.

DETAILED DESCRIPTION OF THE EMBODIMENTS

Figure 1:
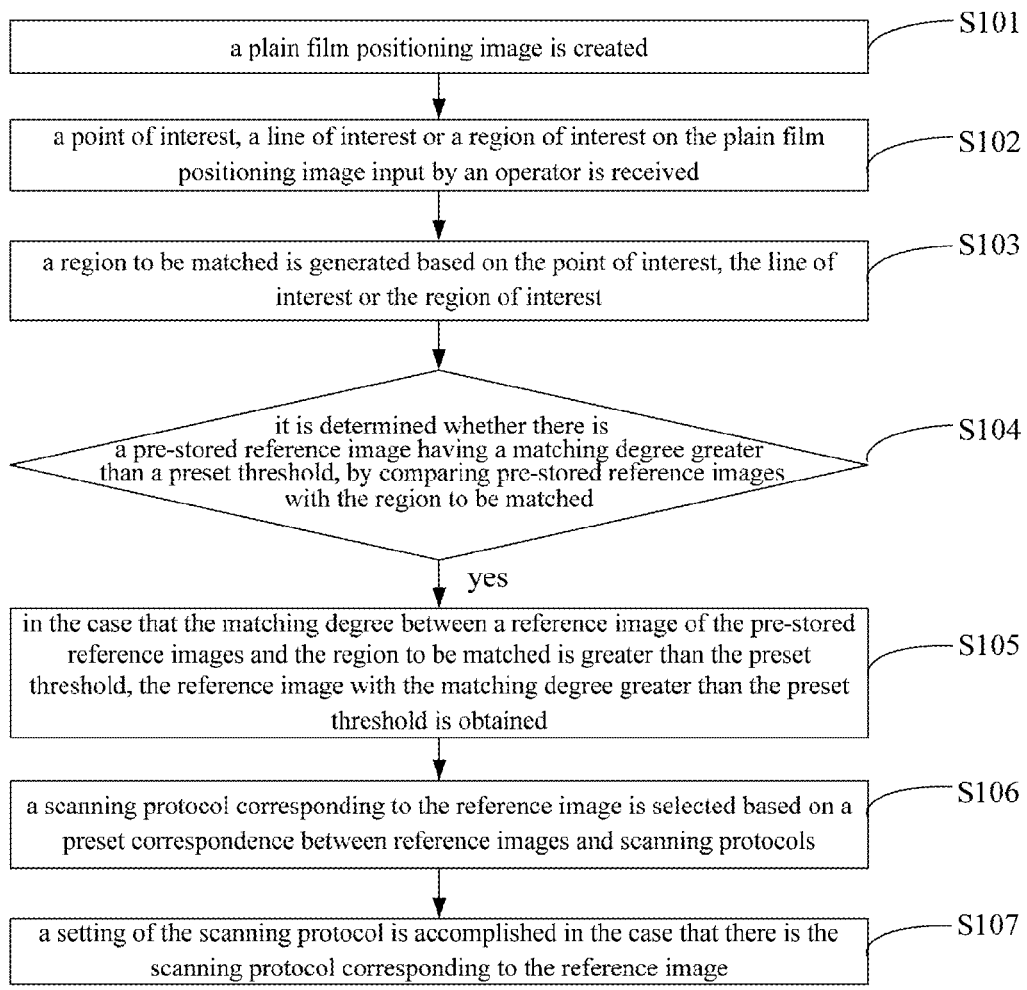
FIG. 1 is a flowchart of a method for setting a scanning protocol according to an example of the present disclosure.

FIG. 1 is a flowchart of a method for setting a scanning protocol according to an example of the present disclosure. The method may include block S101 to block S107.

In block S101, a plain film positioning image is created.

In the example, a plain film positioning image is created firstly. Specifically, the plain film positioning image may be created by performing a plain film scanning on a patient.

In block S102, a point of interest, a line of interest or a region of interest on the plain film positioning image input by an operator is received.

In the example, after the plain film positioning image is created, the operator determines, according to a point of interest, a line of interest or a region of interest (ROI) on the plain film positioning image by an input device such as a mouse. The point of interest, the line of interest or the region of interest is a target or a region close to the target on which the user expects to perform a scanning to diagnose.

In block S103, a region to be matched is generated based on the point of interest, the line of interest or the region of interest.

In the example, the region to be matched is generated based on the point of interest, the line of interest or the region of interest after the point of interest, the line of interest or the region of interest input by an operator is received.

In practice, the size of the point of interest, the line of interest or the region of interest originally input by an operator may not be suitable for a subsequent retrieval of a standard image; hence, in the example, the point of interest, the line of interest or the region of interest input by the operator may function as a seed region, and the size of the seed region automatically adjusts (enlarges or diminishes) with a certain region increasing step (or a certain region decreasing step) to generate the region to be matched.

In block S104, it is determined whether there is a pre-stored reference image having a matching degree greater than a preset threshold, by comparing pre-stored reference images with the region to be matched.

Figure 2:
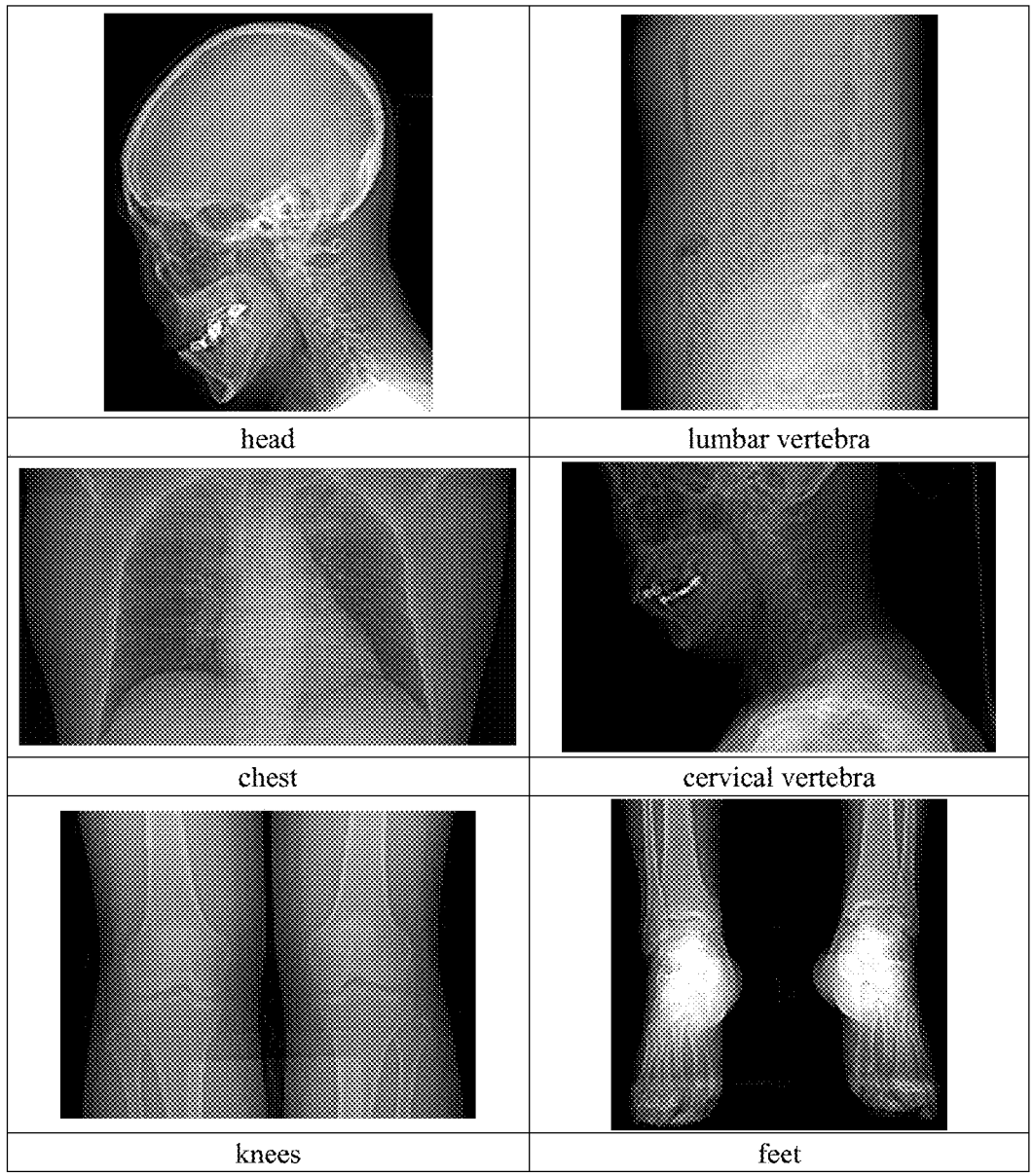
FIG. 2 are reference images of a head, a lumbar vertebra, a chest, a cervical vertebra, knees and feet according to an example of the present disclosure.

In the example, some reference images are stored in advance. For example, reference is made to FIG. 2, which shows respective reference images of a head, a lumbar vertebra, a chest, a cervical vertebra, knees and feet. After a region to be matched is generated, it is determined whether there is a pre-stored reference image having a matching degree greater than a preset threshold, by comparing pre-stored reference images with the region to be matched.

In practice, after a region to be matched is generated through a certain region adjustment based on a determined seed region, firstly, matching degrees between the region to be matched and the respective pre-stored reference images are calculated; then a reference image with a matching degree greater than the preset threshold is obtained. In the case that no reference image has a matching degree greater than the preset threshold, the region to be matched is further taken as a seed region, and a new region to be matched is generated through a certain region adjustment. The matching for the region to be matched is completed until it is determined that a matching degree between a reference image and the region to be matched is greater than the preset threshold.

In the example, the CT system needs to determine a true intension of the operator, i.e., a target region on which the operator truly wants to perform a scanning, based on the fuzzy input of the operator.

In block S105, in the case that the matching degree between a reference image of the pre-stored reference images and the region to be matched is greater than the preset threshold, the reference image with the matching degree greater than the preset threshold is obtained.

In the example, if it is determined that the matching degree between a reference image of the pre-stored reference images and the region to be matched is greater than the preset threshold, the number of the reference image having the matching degree greater than the preset threshold is determined.

In the case that one reference image of the pre-stored reference images has the matching degree greater than the preset threshold, the one reference image is directly obtained.

In the case that multiple reference images have matching degrees greater than the preset threshold, the multiple reference images may be directly displayed to the operator, or names or identifiers of the multiple reference images may be displayed to the operator. The operator may select one of the reference images as the best-matched reference image based on the displayed information. In a particular case where the reference images having matching degrees greater than the preset threshold belong to a same category, for example, a category of the chest, the name of the category may be directly displayed to the operator, and the operator may select an required reference image from the reference images corresponding to various category names based on the displayed category name.

In another example, in the case that multiple reference images have matching degrees greater than the preset threshold, the matching degrees between the multiple reference images and the region to be matched may be calculated respectively and the reference images are sequenced by values of the matching degrees, and a reference image with a highest matching degree is finally obtained.

In the case that the reference image with the highest matching degree does not correspond to a region which the operator really wants to scan, a proper reference image is to be selected from reference images with lower matching degrees based on the sequence of the reference images. For example, for a plain film positioning image for the chest, the operator really wants to scan the lung but a seed region input by the user may be close to the heart; consequently, the reference image with the highest matching degree may be a heart reference image while the matching degree of a lung reference image may be lower than that of the heart reference image.

In block S106, a scanning protocol corresponding to the reference image is selected based on a preset correspondence between reference images and scanning protocols.

In the example, after a reference image best-matched with the region to be matched is determined, a scanning protocol corresponding to the reference image is searched and selected based on the preset correspondence between the reference images and the scanning protocols.

Specifically, the correspondence between the reference images and the scanning protocols is set in the CT system in advance. The scanning protocol includes a coordinate parameter of a scanning region.

In block S107, a setting of the scanning protocol is accomplished in the case that there is the scanning protocol corresponding to the reference image.

In the example, if it is determined that there is one scanning protocol corresponding to the reference image, the scanning protocol may be directly set as a scanning protocol for the patient.

In another example if it is determined that multiple scanning protocols correspond to the reference image, the operator may select one scanning protocol from the multiple scanning protocols and set the selected scanning protocol as the scanning protocol for the patient.

In the present disclosure, firstly the plain film positioning image is created; the point of interest, the line of interest or the region of interest on the plain film positioning image input by an operator is received, and the region to be matched is generated based on the point of interest, the line of interest or the region of interest; and then, the reference image matching the generated region to be matched is determined based on the region to be matched, and finally the scanning protocol corresponding to the reference image is set as the scanning protocol for the patient. Compared with the conventional technology, according to the present disclosure, time for setting the scanning protocol can be saved and efficiency in setting the scanning protocol can be improved. In addition, according to the present disclosure, the scanning protocol is set more accurately.

Figure 3:
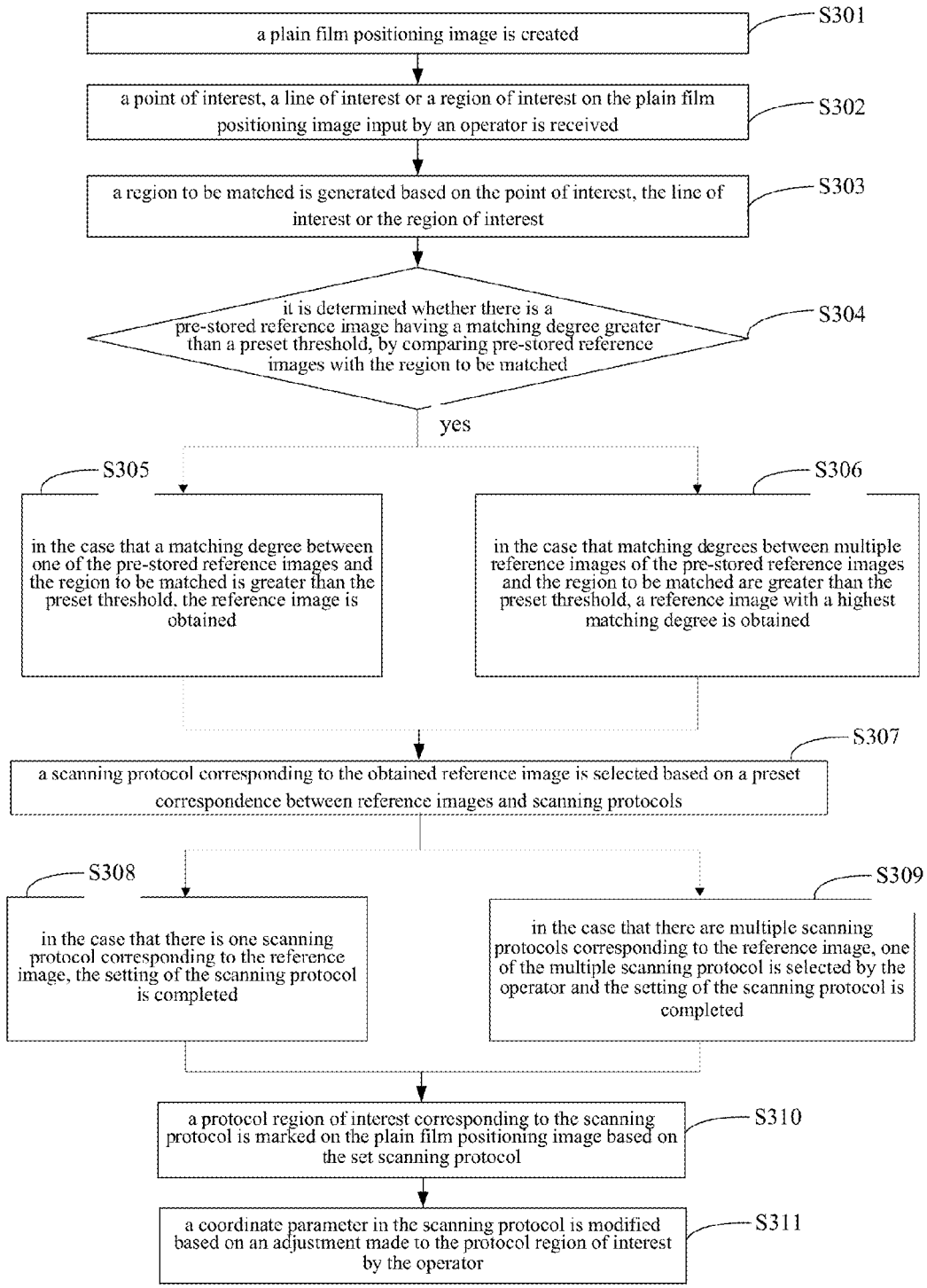
FIG. 3 is a flowchart of a method for setting a scanning protocol according to another example of the present disclosure.

FIG. 3 is a flowchart of a method for setting a scanning protocol according to another example of the present disclosure. The method includes block S301 to block S311.

In block S301, a plain film positioning image is created.

In block S302, a point of interest, a line of interest or a region of interest on the plain film positioning image input by an operator is received.

In block S303, a region to be matched is generated based on the point of interest, the line of interest or the region of interest.

In block S304, it is determined whether there is a pre-stored reference image having a matching degree greater than a preset threshold, by comparing pre-stored reference images with the region to be matched.

In block S305, in the case that a matching degree between one of the pre-stored reference images and the region to be matched is greater than the preset threshold, the reference image is obtained.

In block S306, in the case that matching degrees between multiple reference images of the pre-stored reference images and the region to be matched are greater than the preset threshold, a reference image with a highest matching degree is obtained.

In block S307, a scanning protocol corresponding to the obtained reference image is selected based on a preset correspondence between reference images and scanning protocols.

In block S308, in the case that there is one scanning protocol corresponding to the reference image, the setting of the scanning protocol is completed.

In block S309, in the case that there are multiple scanning protocols corresponding to the reference image, one of the multiple scanning protocol is selected by the operator and the setting of the scanning protocol is completed.

In block S310, a protocol region of interest corresponding to the scanning protocol is marked on the plain film positioning image based on the set scanning protocol.

In block S311, a coordinate parameter in the scanning protocol is modified based on an adjustment made to the protocol region of interest by the operator.

Figure 4:
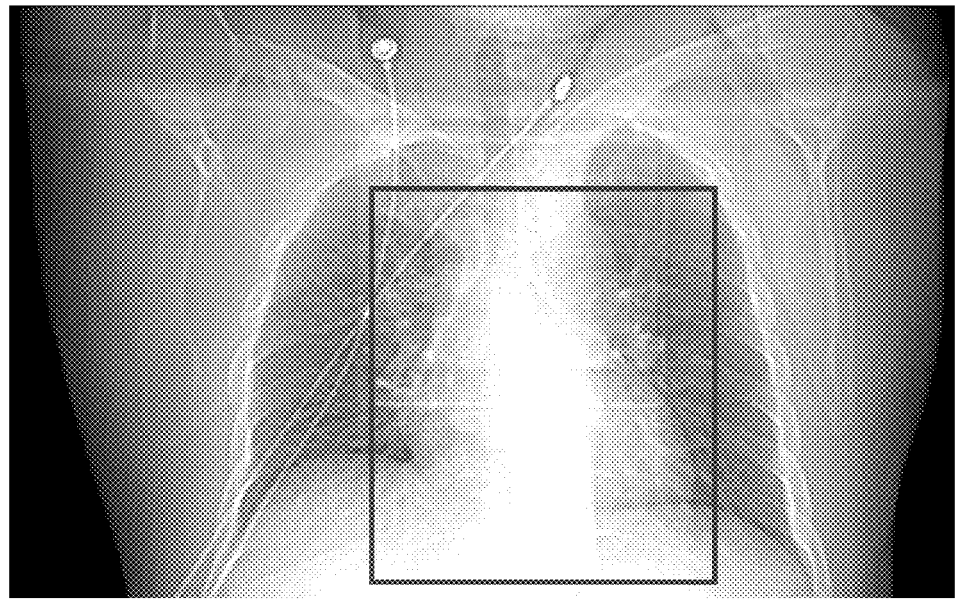
FIG. 4 is a schematic diagram of a protocol region of interest marked by a rectangular block according to the example illustrated in FIG. 3 of the present disclosure.

In the example, after the scanning protocol is set, a rectangular block is automatically drawn on the plain film positioning image based on the set scanning protocol. As shown in FIG. 4, a Protocol Region Of Interest (PROI) is marked with the rectangular block. That is to say, the PROI is determined by the CT system based on a parameter in the scanning protocol, where the parameter includes coordinate information of the PROI.

If the operator finds that the PROI displayed on the plain film positioning image can not accurately indicate the location of the operator interest, the operator may adjust the PROI, i.e., may adjust coordinates of the PROI. After the coordinates of the PROI are adjusted, the coordinate parameter in the scanning protocol may be modified to be in accordance with the adjustment to the PROI.

In practice, the PROI is more accurate than the ROI, and is more close to a specific part where the operator really wants to scan. For example, the ROI is a leg, while the PROI determined based on the set scanning protocol may be limited at a region around a knee-joint. In addition, the set scanning protocol better conforms to scanning requirement of the user with the adjustment made to the PROI by the operator.

In the example, reference images are set in advance and the correspondence between the reference images and the scanning protocols is set in advance; the reference image matching one region to be matched is determined after the region to be matched is obtained; and the scanning protocol corresponding to the reference image is determined, and finally the setting of the scanning protocol is completed. According to the example, a suitable scanning protocol can be determined intelligently, time for setting the scanning protocol can be saved and efficiency in setting the scanning protocol can be improved. Furthermore, in the method for setting the scanning protocol according to the example, a more accurate scanning protocol is set for the patient based on the point of interest, the line of interest or the region of interest input by the operator. In addition, various fine adjustments may be performed on the parameter in the set scanning protocol for more diagnosing objects, that is to say, the parameter of the scanning protocol may be set more finely in the embodiment, thereby improving the conformity of the scanning protocol.

Figure 5:
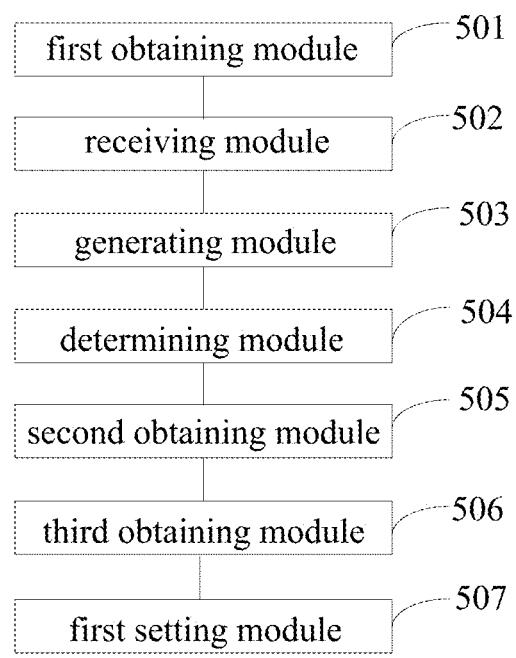
FIG. 5 is a structural diagram of an apparatus for setting a scanning protocol according to an example of the present disclosure.

FIG. 5 is a schematic structural diagram of an apparatus for setting a scanning protocol according to an example of the present disclosure. The apparatus may include a first obtaining module 501, a receiving module 502, a generating module 50, a determining module 504, a second obtaining module 505, a third obtaining module 506 and a first setting module 507.

The first obtaining module 501 is configured to create a plain film positioning image.

The receiving module 502 is configured to receive a point of interest, a line of interest or a region of interest on the plain film positioning image input by an operator.

The generating module 503 is configured to generate, based on the point of interest, the line of interest or the region of interest, a region to be matched.

The determining module 504 is configured to determine whether there is a pre-stored reference image having a matching degree greater than a preset threshold, by comparing pre-stored reference images with the region to be matched.

The second obtaining module 505 is configured to obtain a reference image if the determining module determines that the matching degree between the reference image and the region to be matched is greater than the preset threshold.

The third obtaining module 506 is configured to select a scanning protocol corresponding to the reference image based on a preset correspondence between reference images and scanning protocols.

The first setting module 507 is configured to complete the setting of the scanning protocol in the case that there is one scanning protocol corresponding to the reference image.

In another example, the apparatus may further include a fifth obtaining module.

The fifth obtaining module is configured to obtain a reference image with a highest matching degree in the case that matching degrees between multiple reference images and the region to be matched are greater than the preset threshold.

The apparatus may further include:

a sixth obtaining module, configured to obtain one reference image selected by the operator from multiple reference images in the case that the matching degrees between the multiple reference images and the region to be matched are greater than the preset threshold.

The apparatus may further include:

a second setting module, which is configured to, receive one scanning protocol selected by the user from multiple scanning protocols in the case that the multiple scanning protocols each correspond to the reference image, and complete the setting of the scanning protocol.

In practice, in order to make the set scanning protocol better conform to scanning requirement of the operator, the apparatus may further include a marking module and a modifying module.

The marking module is configured to mark a protocol region of interest corresponding to the scanning protocol on the plain film positioning image based on the set scanning protocol.

The modifying module is configured to modify a coordinate parameter in the scanning protocol based on an adjustment made to the protocol region of interest by the operator.

According to the embodiment, time for setting the scanning protocol can be saved, and efficiency in setting the scanning protocol can be improved. In addition, according to the embodiment, the scanning protocol is set more accurately. In addition, the set scanning protocol may better conform to scanning requirement of the operator with the adjustment made by the operator the PROI.

The apparatus embodiment substantially corresponds to the method embodiment, so the related parts between the apparatus embodiment and the method embodiment may be understood with reference to the illustration of the method embodiment. The apparatus embodiment described above is only exemplary, units illustrated as separate components may be physically separated or not. Components displayed as units may be physical units or not, i.e., the components may locate at one location or may be distributed on multiple network units. Part or all of the modules may be selected to implement the solutions of the embodiment based on actual requirement. Those skilled in the art may understand and implement the disclosure without any creative work.

It should be noted that the relationship terminologies such as "first", "second" and the like are only used herein to distinguish one entity or operation from another, rather than to necessitate or imply that an actual relationship or order exists between the entities or operations. Furthermore, terms of "include", "comprise" or any other variants are intended to be non-exclusive. Therefore, a process, method, article or device including a plurality of elements includes not only the disclosed elements but also other elements that are not clearly enumerated, or also include inherent elements of the process, method, article or device. Unless expressively limited otherwise, the statement "including a . . . " does not exclude the case that other similar elements may exist in the process, method, article or device other than enumerated elements.

The method for setting the scanning protocol and the apparatus thereof according to the embodiments of the disclosure are introduced in detail above, the principles and implementing ways of the disclosure are clarified by specific examples, and the above illustration of the embodiments is only to help to understand the method and key idea of disclosure. In addition, those skilled in the art may make changes to the specific embodiments and the application scope based on the idea of the disclosure. In summary, the specification should not be understood as limitations to the disclosure.

The invention claimed is:

1. A method for setting a scanning protocol, comprising:
creating a plain film positioning image;
receiving a point of interest, a line of interest or a region of interest on the plain film positioning image input by an operator;
generating a region to be matched, based on the point of interest, the line of interest or the region of interest;
determining whether there is a pre-stored reference image having a matching degree greater than a preset threshold, by comparing pre-stored reference images with the region to be matched;
obtaining a reference image in the case that a matching degree between the reference image and the region to be matched is greater than the preset threshold;
selecting a scanning protocol corresponding to the reference image based on a preset correspondence between reference images and scanning protocols; and
completing a setting of the scanning protocol in the case that there is the scanning protocol corresponding to the reference image.

2. The method according to claim 1, further comprising:
obtaining a reference image with a highest matching degree, in the case that the matching degrees between a plurality of reference images and the region to be matched are greater than the preset threshold.

3. The method according to claim 1, further comprising:
obtaining one reference image selected by the operator from a plurality of reference images, in the case that matching degrees between the plurality of reference images and the region to be matched are greater than the preset threshold.

4. The method according to claim 1, further comprising:
selecting one scanning protocol, by the operator, from a plurality of scanning protocols and completing a setting of the scanning protocol, in the case that the plurality of scanning protocols correspond to the reference image.

5. The method according to claim 1, further comprising:
marking, based on the set scanning protocol, a protocol region of interest corresponding to the scanning protocol on the plain film positioning image; and
modifying, based on an adjustment made to the protocol region of interest by the operator, a coordinate parameter of the scanning protocol.

6. An apparatus for setting a scanning protocol, comprising:
a first obtaining module configured to create a plain film positioning image;
a receiving module configured to receive a point of interest, a line of interest or a region of interest on the plain film positioning image input by an operator;
a generating module configured to generate, based on the point of interest, the line of interest or the region of interest, a region to be matched;
a determining module configured to determine whether there is a pre-stored reference image having a matching degree greater than a preset threshold by comparing pre-stored reference images with the region to be matched;
a second obtaining module configured to obtain a reference image if the determining module determines that a matching degree between the reference image and the region to be matched is greater than the preset threshold;
a third obtaining module configured to select a scanning protocol corresponding to the reference image based on a preset correspondence between reference images and scanning protocols; and
a first setting module configured to complete a setting of the scanning protocol in the case that there is the scanning protocol corresponding to the reference image.

7. The apparatus according to claim 6, further comprising:
a fourth obtaining module configured to obtain a reference image with a highest matching degree in the case that matching degrees between a plurality of reference images and the region to be matched are greater than the preset threshold.

8. The apparatus according to claim 6, further comprising:
a fourth obtaining module configured to obtain one reference image selected by the operator from a plurality of reference images in the case that matching degrees between the plurality of reference images and the region to be matched are greater than the preset threshold.

9. The apparatus according to claim 6, further comprising:
a second setting module configured to receive one scanning protocol selected by the operator from a plurality of scanning protocols and complete a setting of the scanning protocol, in the case that the plurality of scanning protocols correspond to the reference image.

10. The apparatus according to claim 6, further comprising:
a marking module configured to mark, based on the set scanning protocol, a protocol region of interest corresponding to the scanning protocol on the plain film positioning image; and
a modifying module configured to modify, based on an adjustment made to the protocol region of interest by the operator, a coordinate parameter of the scanning protocol.

* * * * *